United States Patent
Mikkonen et al.

(10) Patent No.: US 11,135,085 B2
(45) Date of Patent: Oct. 5, 2021

(54) INSERTER FOR AN INTRAUTERINE SYSTEM

(71) Applicant: BAYER OY, Turku (FI)

(72) Inventors: Joonas Mikkonen, Lempäälä (FI); Tero Jalkanen, Turku (FI); Mikko Virtanen, Halikko (FI); Taina Tjäder, Piispanristi (FI); Karym El Sayed, Berlin (DE)

(73) Assignee: BAYER OY, Turku (FI)

( * ) Notice: Subject to any disclaimer, the term of this patent is extended or adjusted under 35 U.S.C. 154(b) by 180 days.

(21) Appl. No.: 16/341,044

(22) PCT Filed: Oct. 10, 2017

(86) PCT No.: PCT/EP2017/075759
§ 371 (c)(1),
(2) Date: Apr. 10, 2019

(87) PCT Pub. No.: WO2018/069285
PCT Pub. Date: Apr. 19, 2018

(65) Prior Publication Data
US 2019/0231588 A1    Aug. 1, 2019

Related U.S. Application Data

(60) Provisional application No. 62/406,650, filed on Oct. 11, 2016.

(51) Int. Cl.
*A61F 6/18*        (2006.01)
*A61F 6/14*        (2006.01)
*A61B 90/00*       (2016.01)

(52) U.S. Cl.
CPC .............. *A61F 6/18* (2013.01); *A61F 6/144* (2013.01); *A61B 2090/062* (2016.02); *A61B 2090/0811* (2016.02)

(58) Field of Classification Search
CPC .. A61F 6/144; A61F 6/142; A61F 6/18; A61F 2/0004; A61F 2/0009;
(Continued)

(56) References Cited

U.S. PATENT DOCUMENTS 9,668,912 B2 *  6/2017  Jutila .................... A61F 6/18

FOREIGN PATENT DOCUMENTS

EP      2772206 A2    9/2014
WO   2007137304 A2   11/2007
(Continued)

OTHER PUBLICATIONS

"International Preliminary Report on Patentability, PCT App. No. PCT/EP2017/075759", dated Apr. 25, 2019.
(Continued)

*Primary Examiner* — Ophelia A Hawthorne (57) ABSTRACT

Disclosed are an inserter and an inserter kit for an intrauterine system. The inserter comprises an insertion tube having a first end and an opposite second end, wherein the first end is operable to removably receive the intrauterine system and a handle having a first end portion and an opposite second end portion, the first end portion of the handle is coupled to the second end of the insertion tube. The handle comprises a handling mechanism for controlling movement of the insertion tube with respect to the intrauterine system. The inserter also comprises an indicating mechanism operatively arranged in connection with the insertion tube and the handle, the indicating mechanism is communicably coupled to the handling mechanism and is operable to provide indicative signals corresponding to operational stages of the inserter. The indicative signals comprise at least one light signal and the indicating mechanism comprises a power source.

15 Claims, 4 Drawing Sheets

(58) Field of Classification Search
CPC .......... A61F 2/0031; A61F 2/005; A61F 6/00; A61F 6/14; A61K 9/0039; A61K 9/0036; A61M 31/002; A61B 2090/062; A61B 2090/0811
See application file for complete search history.

(56) References Cited

FOREIGN PATENT DOCUMENTS

| | | |
|---|---|---|
| WO | 2010031900 A1 | 3/2010 |
| WO | 2016125176 A1 | 8/2016 |

OTHER PUBLICATIONS

"International Search Report of PCT App. No. PCT/EP2017/075759", dated Jan. 10, 2018.

* cited by examiner

INSERTER FOR AN INTRAUTERINE SYSTEM

CROSS REFERENCE TO RELATED APPLICATIONS

This application is a National Phase application under 35 U.S.C. § 371 of International Application No. PCT/EP2017/075759, filed Oct. 10, 2017, which claims priority benefit of U.S. Provisional Application No. 62/406,650, filed Oct. 11, 2016.

TECHNICAL FIELD

The present disclosure generally relates to a medical device, and more specifically to an inserter for an intrauterine system.

BACKGROUND

Use of an intrauterine system (IUS) is a known method of contraception, and IUS's can also be used for other needs of local administration of therapeutically active agents. Further, proper functioning of an intrauterine system depends on the accurate placement of the intrauterine system in a uterus. An inserter may be used to place an intrauterine system into the uterus. Typically, prior to insertion, the intrauterine system is at least essentially placed inside an insertion tube of the inserter, and in case the intrauterine system has a T-shape, its two arms are folded within the insertion tube. Thereafter, the insertion tube is inserted into the uterine cavity, the intrauterine system is released in the uterine cavity, and the insertion tube is removed from the uterine cavity.

Typically, a process of insertion of an intrauterine system includes various operational stages of the inserter, and accordingly requires an experienced medical practitioner to accurately perform such operational stages of the inserter. For example, the insertion tube of the inserter is required to be precisely moved with respect to a depth of the uterine cavity while inserting the intrauterine system. Further, the inserter is operated to release the intrauterine system in the uterine cavity. The intrauterine system is not visible from outside during insertion, and therefore it may be difficult to observe if the intrauterine system is completely expulsed from the inserter. Therefore, a medical practitioner may not be able to correctly observe if the intrauterine system is properly placed inside the uterine cavity.

In some cases, for example with intrauterine systems having a T-shaped body, the IUS cannot be stored inside the inserter for a long period of time. Indeed, the arms of the IUS might not open again, if they were folded for a long time. Thus the practitioner may need to firstly enter the IUS inside (or at least essentially inside) the inserter, before insertion.

Therefore, in light of the foregoing discussion, there exists a need to overcome the aforementioned drawbacks associated with insertion of an intrauterine system.

SUMMARY

The present disclosure seeks to provide an inserter for an intrauterine system. The present disclosure also seeks to provide an inserter kit. The present disclosure seeks to provide a solution to the existing problem of authentication of proper functioning of an inserter and poor visibility for insertion process. An aim of the present disclosure is to provide a solution that overcomes at least partially the problems encountered in the prior art and assists in efficiently handling an inserter for inserting an intrauterine system.

In some embodiments, the present disclosure provides an inserter for an intrauterine system, the inserter comprising:
  an insertion tube having a first end and an opposite second end, wherein the first end is operable to removably receive the intrauterine system;
  a handle having a first end portion and an opposite second end portion, the first end portion of the handle being coupled to the second end of the insertion tube, wherein the handle comprises a handling mechanism for controlling movement of the insertion tube with respect to the intrauterine system; and
  an indicating mechanism operatively arranged in connection with the insertion tube and the handle, wherein the indicating mechanism is communicably coupled to the handling mechanism and is operable to provide indicative signals corresponding to operational stages of the inserter, and wherein the indicative signals comprise at least one light signal and the indicating mechanism comprises a power source.

In some embodiments, the present disclosure provides an inserter kit, the inserter kit comprising:
  an inserter for an intrauterine system comprising
  an insertion tube having a first end and an opposite second end, wherein the first end is operable to removably receive the intrauterine system;
  a handle having a first end portion and an opposite second end portion, the first end portion of the handle being coupled to the second end of the insertion tube, wherein the handle comprises a handling mechanism for controlling movement of the insertion tube with respect to the intrauterine system; and
  an indicating mechanism operatively arranged in connection with the insertion tube and the handle, wherein the indicating mechanism is communicably coupled to the handling mechanism and operable to provide indicative signals corresponding to operational stages of the inserter, and wherein the indicative signals comprise at least one light signal;
  a power source; and
  a charging station comprising a charging dock operable to be removably coupled with the power source for charging the power source using a power supply.

Embodiments of the present disclosure substantially eliminate or at least partially address the aforementioned problems in the prior art. In some embodiments, an inserter is provided, the inserter having an indicating mechanism operable to authenticate various operational stages of the inserter while inserting an intrauterine system.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In some embodiments, the present disclosure provides an inserter for an intrauterine system, the inserter comprising:
- an insertion tube having a first end and an opposite second end, wherein the first end is operable to removably receive the intrauterine system;
- a handle having a first end portion and an opposite second end portion, the first end portion of the handle being coupled to the second end of the insertion tube, wherein the handle comprises a handling mechanism for controlling movement of the insertion tube with respect to the intrauterine system; and
- an indicating mechanism operatively arranged in connection with the insertion tube and the handle, wherein the indicating mechanism is communicably coupled to the handling mechanism and is operable to provide indicative signals corresponding to operational stages of the inserter, and wherein the indicative signals comprise at least one light signal and the indicating mechanism comprises a power source.

In the present description, by first ends are meant typically the ends that are closer to the uterus during insertion, while the second ends are the distal ends, i.e. closer to the user of the inserter, such as the medical practitioner.

The present disclosure provides an inserter and an inserter kit (having an inserter) for efficiently performing a process of inserting an intrauterine system into a uterine cavity of a uterus. In some embodiments, inserter includes an indicating mechanism operable to produce indicative signals (i.e. light and optionally sound signals) based on operational stages of the inserter. Therefore, the indicating mechanism may enable in authenticating ongoing and completed operational stages of the inserter, which enables a medical practitioner to efficiently guide or handle the inserter to insert the intrauterine system. For example, the use of an indicating mechanism makes the process of inserting an intrauterine system less cumbersome by approving the actions performed by the medical practitioner with the help of indicative signals. Further, the use of an indicating mechanism may enable in reducing a time taken for the process of inserting the intrauterine system. Moreover, the use of an indicating mechanism may enable in increasing an overall rate of successful insertion of the intrauterine system.

In some embodiments, the inserter may be an easy to use device for inserting the intrauterine system. In some embodiments, the intrauterine system may be at least partially pre-installed in the inserter, and therefore manual intervention for arranging the intrauterine system in the inserter is avoided. As explained above, the IUS may not be completely pre-installed in the inserter but the inserter needs to be actioned for the IUS to be arranged in the inserter and ready for insertion.

In some embodiments, the inserter comprises an insertion tube. The insertion tube includes a first end and an opposite second end. In some embodiments, the first end of the insertion tube is operable to removably receive the intrauterine system. For example, the intrauterine system may be at least partially pre-installed in the first end of the insertion tube of the inserter. In some embodiments, the insertion tube is a hollow elongated tubular structure. Specifically, the insertion tube may include an opening running through the entire length from the first end to the second end. Accordingly, the insertion tube has an outer diameter and an inner diameter. In some embodiments, the inner diameter is dimensioned to receive the intrauterine system therein.

In some embodiments, the insertion tube may be made of medical grade transparent material, such as transparent plastic. For example, the insertion tube may be made of polyethylene, polypropylene or the like.

In some embodiments, the insertion tube may comprise at least one optical fiber. The optical fiber may enable in illuminating the insertion tube, explained in greater detail herein later. The optical fiber may be placed within the insertion tube between outer and inner surface thereof. In some embodiments, a plurality of optical fibers may be arranged uniformly within tubular structure of the insertion tube.

In some embodiments, the insertion tube may comprise plurality of markings on its outer surface to measure a depth of an insertion to be made by the insertion tube. For example, the outer surface of the insertion tube has calibrated lines to calculate a depth of the uterine cavity. In some embodiments, the inserter may include a movable flange arranged on the outer surface of the insertion tube. The medical practitioner may use for example an ultrasound probe to determine the depth of the uterus and set the flange at the correct insertion depth.

In some embodiments, the inserter also comprises a handle having a first end portion and an opposite second end portion. The handle enables in holding the inserter. Further, the first end portion of the handle may be coupled to the second end of the insertion tube. One possible type of inserter is disclosed in WO 2010/031900, the content of which is herein incorporated by reference.

The handle may have various shapes and may be designed for easy handling with a single hand. For example, the handle may be designed to conform to a palm of an operator, such as a medical practitioner.

In some embodiments, the handle comprises a handling mechanism for controlling movement of the insertion tube with respect to the intrauterine system. For example, the handling mechanism controls movement of the insertion tube for retracting and releasing the intrauterine system from within the first end of the insertion tube, and/or it may control the movement of a plunger arranged inside the insertion tube, depending on the type of the inserter used. Further, the handling mechanism may enable in controlling the movement of the insertion tube after being inserted into the uterine cavity. For example, the handling mechanism may be used for insertion, to securely position, and release the intrauterine system into the uterine cavity of the uterus.

In some embodiments, the handling mechanism comprises a control button arranged in the handle. Specifically, the control button may be operable for controlling the movement of the insertion tube and/or of the plunger with respect to the intrauterine system. Moreover, the control button may be used to release the intrauterine system from the insertion tube.

In some embodiments, the inserter comprises a manoeuvring member, such as a plunger, operatively coupled to the control button. Further, the manoeuvring member may comprise a locking means for locking the intrauterine system via the removal string of the intrauterine system. In some embodiments, the locking means may be controlled by the control button, i.e. to retain or release the intrauterine system from the insertion tube.

In some embodiments, the control button for controlling the movement of the insertion tube may be a slider button. Specifically, the slider button may comprise a transversal member such as a knob or switch, for moving the slider button. The handle may comprise one or more means to connect the slider button and to facilitate the movement of the slider button, for example a support, a holder, a saddle, a groove or a slot. Further, the transversal member may be moved in a forward and a backward direction, longitudinal to the handle.

In some embodiments, the inserter further comprises an indicating mechanism operatively arranged in connection with the insertion tube and the handle. Further, the indicating mechanism may be communicably coupled to the handling mechanism and may be operable to provide indicative signals corresponding to operational stages of the inserter. In some embodiments, the indicative signals comprise at least one light signal. Additionally, the indicative signals may also comprise at least one sound signal. The indicative signals may further comprise a vibration of the inserter.

In some embodiments, the indicating mechanism comprises at least one light source arranged in proximity to a connection of the first end portion of the handle and the second end of the insertion tube; a controller unit arranged in the handle, wherein the controller unit is operable to control the at least one light source to provide the at least one light signal corresponding to the operational stages of the inserter; and a power source arranged in the handle to provide electrical power to the at least one light source and the controller unit.

In some embodiments, the indicating mechanism may thus comprise various interconnected electronic components to indicate the operational phases of the inserter. For example, the indicating mechanism may comprise one or more light sources. In some embodiments, the light source may be arranged in proximity to a connection of the first end portion of the handle and the second end of the insertion tube. By proximity is herein meant that the light source may be at the connecting point of the handle and the insertion tube or it may be arranged for example to surround the connecting point. In any case, it is preferably arranged such that when illuminated, the light emitted can illuminate the insertion tube, i.e. that there are no obstacles between the light source and the insertion tube. For example, the emitted light of the light source may be allowed to pass through the optical fiber of the insertion tube to allow the insertion tube to emit the visible light. In some embodiments, the inserter may also comprise more than one light source, for example two, three or four light sources, and they may be arranged at various places of the inserter.

In some embodiments, the at least one light source may be operable to produce at least one light signal to indicate at least one operational phase of the inserter. In some embodiments, the at least one light source comprises at least one light emitting diode (LED), for example one LED or multiple LEDs. Further, the at least one LED may be operable to emit visible light of at least one colour, which may be associated with the indicative signals of the indicative mechanism. For example, the light source may be operable to emit a magenta colour, a green colour or no colour, associated with various operational phases of the inserter. Further, in some embodiments, the at least one light source may be operable to emit the visible light having the at least one colour continuously or intermittently. In some embodiments, the light source may also be operable to emit visible light with different colours, each colour corresponding to an operational stage of the inserter.

In some embodiments, the light source may be thus arranged on the inserter at various locations. For example, it may be arranged on the junction between the handle and the insertion tube. It may also be arranged on the handling mechanism (such as a slider), for example in the form of two parallel arrows that are illuminated. The arrows could for example point to opposite directions, to indicate the required direction of movement of the handling mechanism. It may also be placed on the insertion tube or at the second, distal end of the handle. In some embodiments, the inserter may also comprise more than one light source at various locations of the inserter.

Further, the operational stages of the inserter may include retraction of the intrauterine system at least mainly within the insertion tube; insertion of the insertion tube into the uterine cavity of a uterus to a first insertion depth; a first movement of the insertion tube with respect to the intrauterine system, movement of the insertion tube to a second insertion depth, and a second movement of the insertion tube with respect to the intrauterine system, in order to release the intrauterine system.

According to some embodiments of the present disclosure, the intrauterine system is a T-shaped intrauterine device, i.e. a body with two arms and a capsule comprising a therapeutically active agent arranged on the body. In some embodiments, the intrauterine system may also include a removal string coupled to the body, opposite to the two arms. In some embodiments, the removal string may enable in pulling out inserted intrauterine system from within a uterine cavity for removal or replacement. In this case, the arms of the intrauterine system are released during the first movement of the insertion tube and the second insertion depth is such that the arms of the intrauterine system come into contact with fundus of uterine wall.

In some embodiments, the indicating mechanism may further comprise an audio source to provide the indicative signals (in addition to the light signals) corresponding to the operational stages of the inserter. For example, the audio source may include a speaker arranged in the handle and able to produce at least one sound signal corresponding to the operational stages of the inserter. In an example, the indicative signals produced by the audio source may be a continuous sound or intermittently beeps.

In some embodiments, the indicating mechanism may comprise a controller unit, arranged in the handle. In some embodiments, the controller unit may be operable to control the indicative signals corresponding to the operational stages of the inserter. For example, the controller unit may be operable to control the at least one light source (and/or the sound source) to provide the at least one light signal (and/or the sound signal) corresponding to the operational stages of the inserter. In some embodiments, the controller unit may include electronic components, such as a processor and a memory having executable instructions, for controlling the at least one light source (and/or the sound source) to provide light signals (and/or sound signals) corresponding to the operational stages of the inserter. Further, the controller unit may enable synchronizing the operation of the light and sound sources to provide a synchronized light and sound signal associated with a particular operational stage of the inserter.

In some embodiments, the indicating mechanism may further comprise a power source arranged in the handle to provide electrical power to the at least one light source and the controller unit. The power source may include a battery, such as an AAAA battery or coin cells, designed to provide required electrical power to the at least one light source and the controller unit. According to some embodiments, the power source is arranged as a detachable part of the handle of the inserter. In this case, the handle comprises means for electrically connecting the controller unit and the light source to the power source when it is in place on the handle.

The power source may be an integral part of the inserter, for example it may be arranged in the handle of the device. In another embodiment, the power source is detachable from the inserter, and can be charged in a separate charging dock. It is also possible that all electronic components, such as the power source, the controller unit and the light source are arranged in a detachable part of the inserter, typically a detachable part of the handle. In some embodiments, the light emitted by the light source would then be conveyed to the insertion tube via one or more optical fibres. This embodiment would have the advantage that all the electronic parts are re-usable and furthermore, they do not need to stand as harsh sterilization conditions as the rest of the inserter.

In some embodiments, the inserter needs to be such that it can be sterilised using ethylene oxide sterilisation. The parts thus need to fulfil the requirements of the relevant standard, in Europe the ATEX (appareils destinés à être utilisés en atmosphères explosives) standard. Therefore, the electronic components most likely will need to be coated in order to protect them from the ethylene oxide and moisture during sterilisation.

Furthermore, in case the inserter and its package is not ATEX-approved, and a battery is used as a power source, the battery is not allowed to be inside the device during sterilisation. In this case, the practitioner will place the battery into inserter after taking it off from the package. In case the battery is in place during sterilisation, it may need to be activated by removing a protective film or similar.

According to some embodiments, the controller unit may operable to control the indicative signals based on the handling mechanism For example, the controller unit may provide indicative signal based on the movement of the control button of the handling mechanism.

According to some embodiments, the indicating mechanism comprises at least one light source and the indicating mechanism is operable to
emit visible light having a first colour to indicate the intrauterine system is at least mainly retracted within the insertion tube,
emit the visible light having the first colour continuously to indicate insertion of the insertion tube into the uterine cavity of the uterus to the first insertion depth,
emit intermittently the visible light having the first colour during the first movement of the insertion tube,
emit a visible light having a second colour to indicate insertion of the insertion tube to the second insertion depth, and
stop emitting the visible light having the second colour to indicate release of the intrauterine system in the uterine cavity.

Thus the at least one light source of the indicating mechanism may be operable to emit visible light having a first colour (such as magenta colour) to indicate the intrauterine system is at least mainly retracted within the insertion tube. Further, the at least one light source may emit the visible light having the first colour (such as magenta colour) continuously to indicate insertion of the insertion tube into the uterine cavity of the uterus to the first insertion depth. In such instance, the continuously glowing insertion tube may provide additional light to enable the medical practitioner to properly guide the insertion tube into the uterine cavity. The at least one light source may further emit intermittently (or blinks, i.e. periodically turns ON and OFF) the visible light having the first colour (such as magenta colour) during the first movement of the insertion tube. Moreover, the at least one light source may emit a visible light having a second colour (such as green colour) to indicate insertion of the insertion tube to the second insertion depth. Additionally, the at least one light source may stop emitting the visible light having the second colour (such as green colour) to indicate release of the intrauterine system in the uterine cavity.

In some embodiments, the operational stages of the inserter may be primarily controlled by the handling mechanism of the inserter. For example, the handling mechanism may be used to retract the intrauterine system at least mainly within the insertion tube. For example, the control button may be operable to move the insertion tube (i.e. move forward with respect to the handle) for folding the two arms of the intrauterine device to be completely received into the first end of the insertion tube. Thereafter, the insertion tube may be inserted into a uterine cavity of the uterus to a first insertion depth. Further, the handling mechanism may be used to perform a first movement of the insertion tube with respect to the intrauterine system. For example, the first movement may move the insertion tube (i.e. move backwards with respect to the handle) for discharging or extending the two arms from the first end of the insertion tube and unfold completely. Furthermore, the operational stages may include inserting the insertion tube to a second insertion depth, i.e. the intrauterine system is further moved into the uterine cavity allowing the unfolded arms of the intrauterine system to contact the fundus of the uterine wall. Moreover, the operational stages may include operating the handling mechanism to perform a second movement of the insertion tube with respect to the intrauterine system, in order to release the intrauterine system. For example, the locking means may be controlled by the handling mechanism, i.e. to release the intrauterine system from the insertion tube into the uterine cavity. Thereafter, the insertion tube is withdrawn from the uterus.

In another aspect, an embodiment of the present disclosure provides an inserter kit, the inserter kit comprising:

an inserter for an intrauterine system comprising an insertion tube having a first end and an opposite second end, wherein the first end is operable to removably receive an intrauterine system;

a handle having a first end portion and an opposite second end portion, the first end portion of the handle being coupled to the second end of the insertion tube, wherein the handle comprises a handling mechanism for controlling movement of the insertion tube with respect to the intrauterine system; and an indicating mechanism operatively arranged in connection with the insertion tube and the handle, wherein the indicating mechanism is communicably coupled to the handling mechanism and operable to provide indicative signals corresponding to operational stages of the inserter, and wherein the indicative signals comprise at least one light signal;

a power source; and a charging station comprising a charging dock operable to be removably coupled with the power source for charging the power source using a power supply.

In some embodiments, the inserter of the inserter kit is thus essentially as described above and thus the various embodiments disclosed above apply mutatis mutandis to the inserter kit. In-some embodiments, the power source is arranged in the handle and in another embodiment, the power source is arranged as a detachable part of the handle.

Thus, depending on the embodiment, either the whole inserter can be placed on the charging dock or only the detachable power source of the inserter need to be charged. The latter option may be beneficial especially where a significant number of IUS's are inserted, as the amount of waste and especially of electrical was can thus be reduced. The charging dock as well as the detachable power source naturally need to be built such that they support cleaning in order to ensure hygienic conditions.

The charging dock may comprise a shape conforming to the second end portion of the handle, for example, the charging dock may include a groove conforming to the second end portion of the handle. Further, the second end portion of the handle may snugly fit within the groove of the charging dock. Further, each of the second end portion of the handle and the charging dock may include at least one electrical connector, such as an electrical pin, for establishing electrical connection therebetween.

DETAILED DESCRIPTION OF THE DRAWINGS

Figure 1:
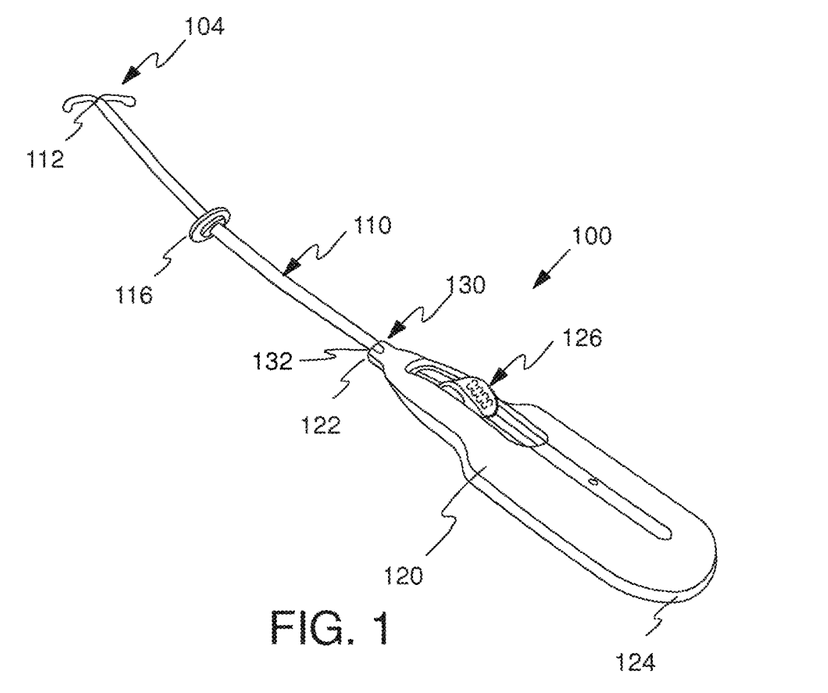
FIG. 1 schematically illustrates an inserter for an intra-uterine system, in accordance with some embodiments of the present disclosure.

FIG. 1 is a perspective view of an inserter 100, in accordance with some embodiments of the present disclosure. The inserter 100 comprises an insertion tube 110. The insertion tube 110 has a first end 112 and an opposite second end 114. The first end 112 is operable to removably receive an intrauterine system 104, in this case a T-shaped intrauterine system having two transverse arms. The intrauterine system 104 is shown partially received by the first end 112 of the insertion tube 110. The inserter 102 further includes a movable flange 116, arranged on the insertion tube 110 for setting the insertion depth.

The inserter 100 also includes a handle 120 having a first end portion 122 and an opposite second end portion 124. The first end portion 122 of the handle 120 is coupled to the second end 114 of the insertion tube 110. The handle 120 includes a handling mechanism 126 for controlling movement of the insertion tube 110 with respect to the intrauterine system 104. As shown, the handling mechanism 126 includes a control button, in this case a slider button, adapted to be manually operated for controlling movement of the insertion tube 110 with respect to the intrauterine system 104.

The inserter 102 also includes an indicating mechanism 130 operatively arranged in connection with the insertion tube 110 and the handle 120, and communicably coupled to the handling mechanism 126, operable to provide indicative signals corresponding to operational stages of the inserter 102. The indicating mechanism 130 includes at least one light source 132, and a controller unit (not shown) arranged inside the handle 120. The controller unit is operable to control the light source 132 to provide the at least one light signal corresponding to the operational stages of the inserter 102. The power source is not shown in the Figure, as it is arranged inside the handle.

Figure 2:
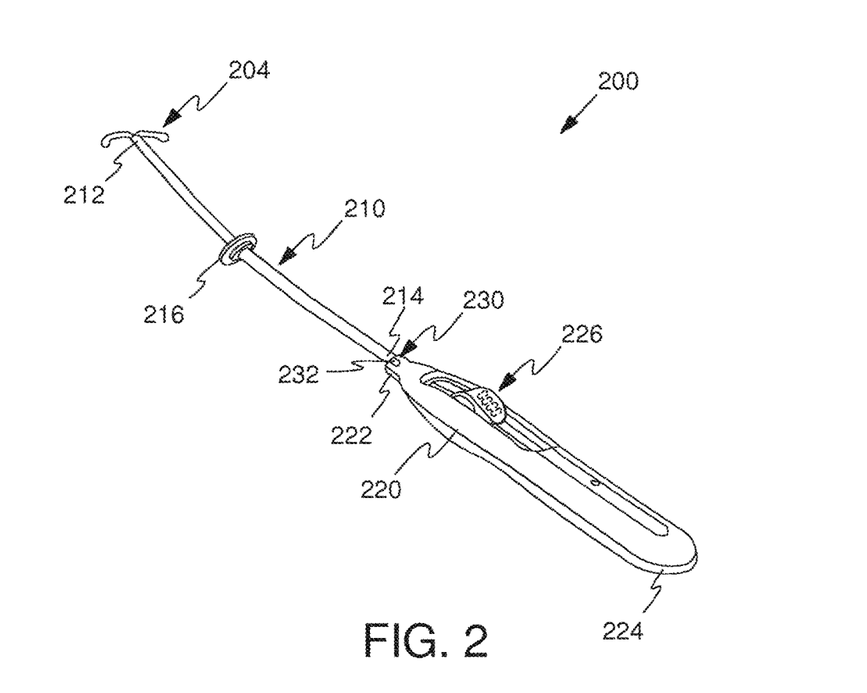
FIG. 2 schematically illustrates an inserter for an intra-uterine system, in accordance with some embodiments of the present disclosure.

FIG. 2 illustrates an inserter according to some embodiments, with the only difference that the power source is a detachable part of the handle, and can thus be charged on its own. The inserter 200 comprises an insertion tube 210, and an intrauterine system 204 is shown partially received by the first end 212 of the insertion tube 110. The inserter 200 also comprises a handle 120 coupled to the insertion tube 210. The handle 220 includes a handling mechanism 226 and an indicating mechanism 230. The indicating mechanism 230 includes at least one light source 232. In some embodiments, the power source is a detachable part and it is not shown in FIG. 2.

Figure 3:
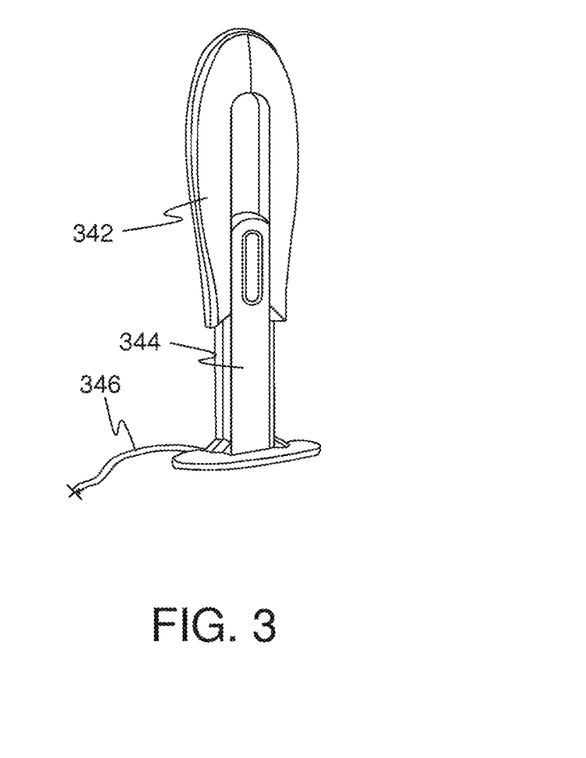
FIG. 3 schematically illustrates a charging dock, in accordance with some embodiments of the present disclosure.

FIG. 3 illustrates a charging dock according to some embodiments of the present description. A detachable power source 342 is arranged on a charging dock 344, which is connected to a source of electricity via a power cable 346.

Figure 4:
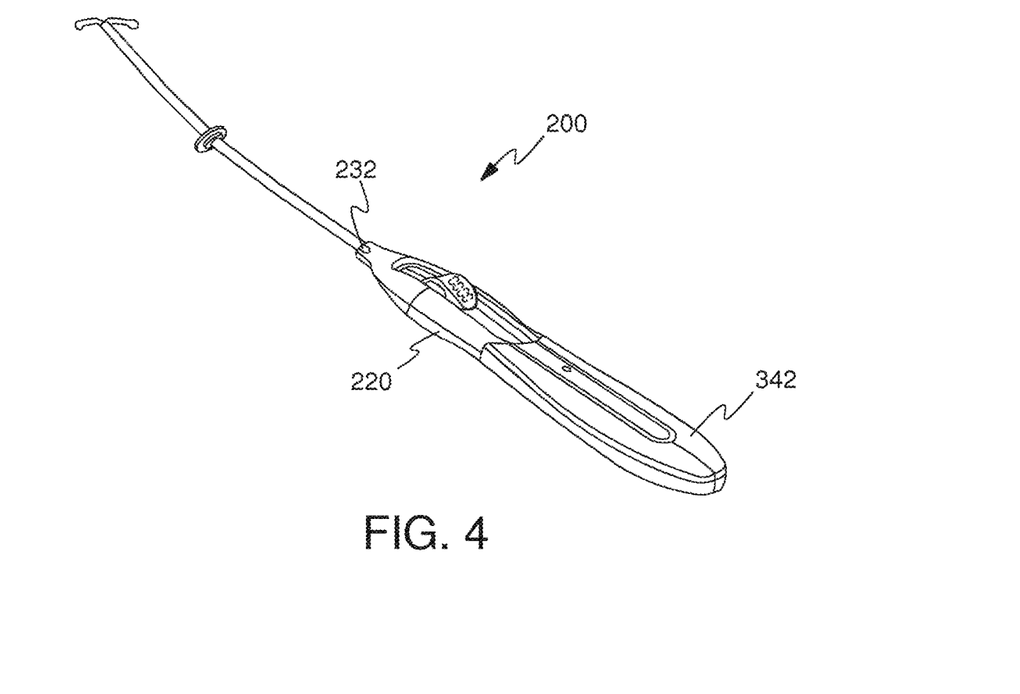
FIG. 4 schematically illustrates the inserter of FIG. 2 with a power source according to some embodiments of the present disclosure.

FIG. 4 is a perspective view of the inserter 202 (shown in FIG. 2) together with the detachable power source 342 according to some embodiments. As shown, the power source 342 is coupled to the second end portion 224 of the handle 220.

FIGS. 5-9 are perspective views of an inserter, such as the inserter 302, depicting various operational stages thereof, in accordance with some embodiments of the present disclosure.

Figure 5:
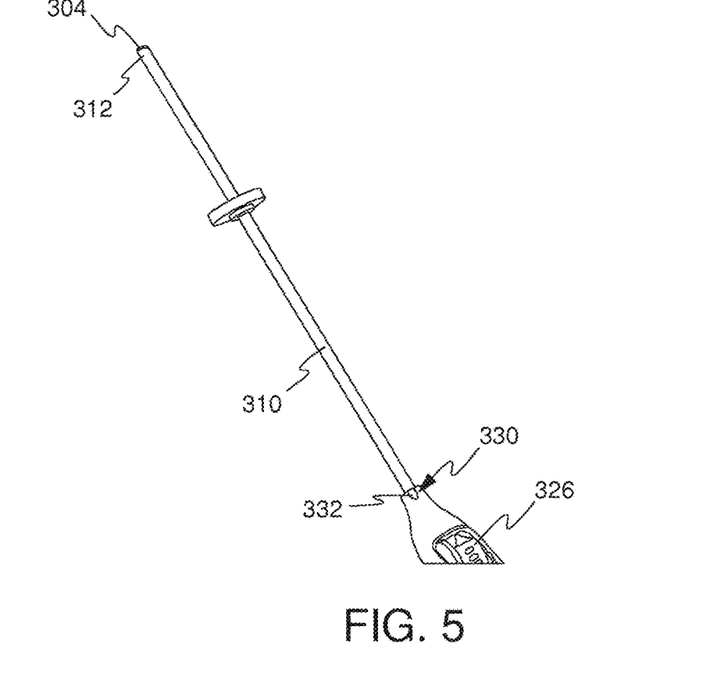
FIGS. 5-9 are perspective views of an inserter depicting various operational stages thereof, in accordance with some embodiments of the present disclosure.

FIG. 5 depicts retraction of the intrauterine system 304 at least mainly within the insertion tube 310 according to some embodiments. Specifically, the pair of arms of the intrauterine system 304 is folded to be almost completely received into the first end 312 of the insertion tube 310. For example, the insertion tube 310 is moved towards the intrauterine system 304, with the help of the handling mechanism 326 (i.e. the slider button), while retaining the intrauterine system 304 in a fixed position. This allows the intrauterine system 304 to be received into the first end 312 of the insertion tube 310. Preferably, the tips of the arms of the intrauterine system slightly protrude from the end of the insertion tube. In such instance, the indicating mechanism 330 is operable to provide an indicative signal, such as a light signal. For example, the light source 332 emits visible light having a first colour (for example magenta) to indicate the intrauterine system 304 is at least mainly retracted within the insertion tube 310. Further, the visible light of the first colour is emitted through the insertion tube 310.

Figure 6:
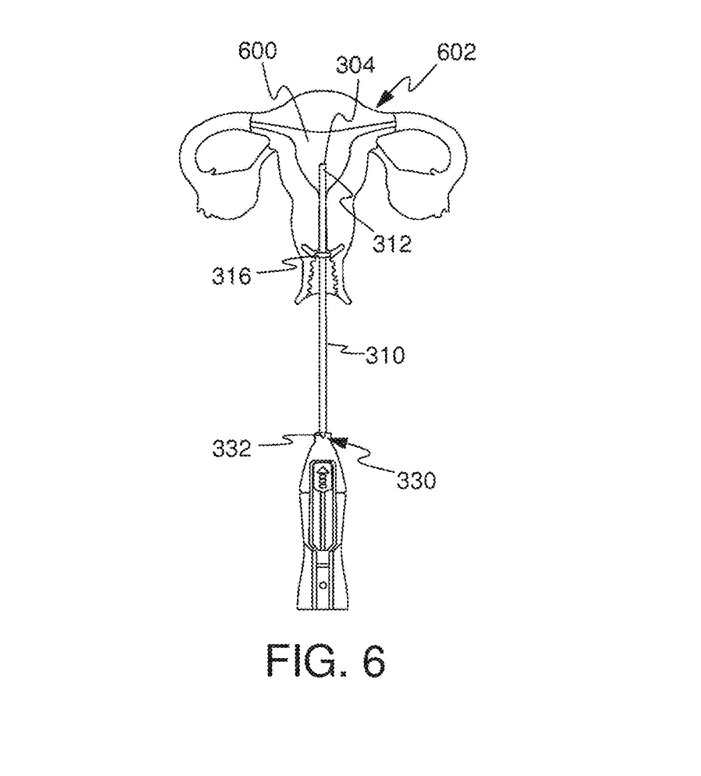

FIG. 6 depicts insertion of the insertion tube 310 into a uterine cavity 600 of a uterus 602 to a first insertion depth according to some embodiments. The first insertion depth of the uterine cavity 600 may be predetermined using the movable flange 316, arranged on the insertion tube 310. As shown, the first insertion depth is an intermediate position in the uterine cavity 600, for example, half way along the uterine cavity 600. Further, the intrauterine system 304 remains inside the first end 312 of the insertion tube 310. In such instance, the indicating mechanism 330 is operable to provide an indicative signal, such as a light signal. For example, the light source 332 emits the visible light having the first colour continuously to indicate insertion of the insertion tube 310 into the uterine cavity 600 of the uterus 602 to the first insertion depth. Further, the visible light of first colour is emitted continuously through the insertion tube 310.

Figure 7:
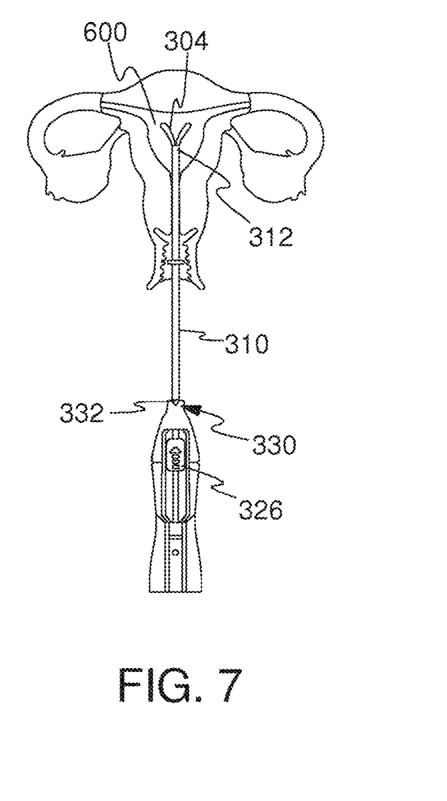

FIG. 7 depicts a first movement of the insertion tube 310 with respect to the intrauterine system 304 according to some embodiments. The first movement includes the slider button 326 to be manually operated for moving the insertion tube 310 with respect to the intrauterine system 304. Specifically, the insertion tube 310 is moved backwards, while keeping the intrauterine system 304 in the fixed position. Therefore, the first movement of the insertion tube 310 causes the intrauterine system 304 to be exposed such that the pair of arms extends out of the first end 312 of insertion tube 310, into the uterine cavity 600. In such instance, the indicating mechanism 330 is operable to provide light signal. For example, the light source 332 emits intermittently (blink ON and OFF continuously) the visible light having the first colour during the first movement of the insertion tube 310. Further, the visible light of first colour is emitted intermittently through the insertion tube 310.

Figure 8:
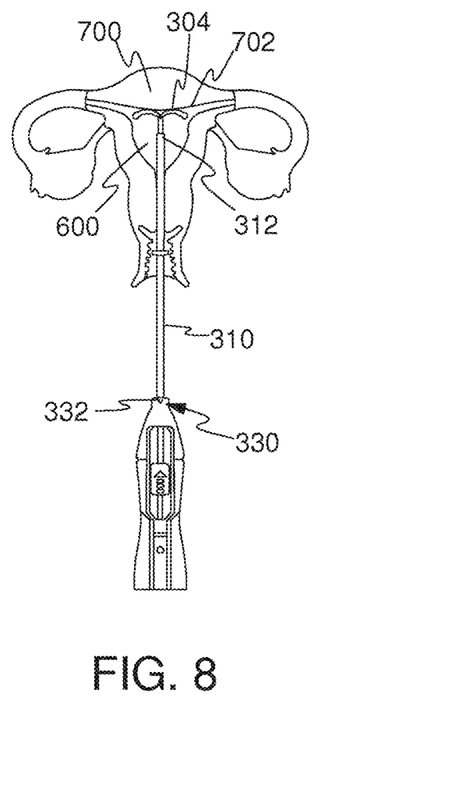

FIG. 8 depicts movement of the insertion tube 310 to a second insertion depth according to some embodiments. Specifically, the second insertion depth is such that the arms of the intrauterine system 304 come into contact with fundus 700 of uterine wall 702. As shown, the first end 312 of the insertion tube 310 is further inserted into the uterine cavity 600 to allow the unfolded pair of arms of the intrauterine system 304 contact the fundus 700 of the uterine wall 702. In such instance, the indicating mechanism 330 is operable to provide light signal. For example, the light source 332 emits a visible light having a second colour to indicate insertion of the insertion tube 310 to the second insertion depth. Further, the visible light of second colour is emitted through the insertion tube 310.

Figure 9:
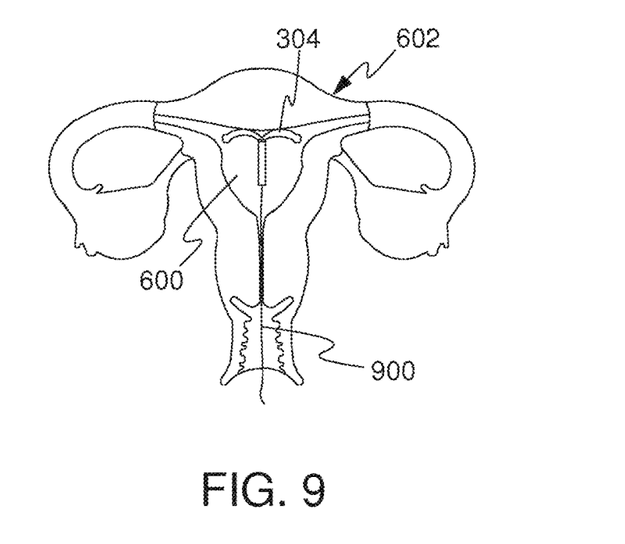

FIG. 9 depicts a second movement of the insertion tube 310 with respect to the intrauterine system 304, in order to release the intrauterine system 304, according to some embodiments. Specifically, the second movement includes releasing the intrauterine system 304 to be inserted into the uterine cavity 600 and withdrawing the insertion tube 310 from the uterus 602. In such instance, the indicating mechanism 330 is operable to provide an indicative signal. For example, the light source 332 stops emitting the visible light having the second colour to indicate release of the intrauterine system 304 in the uterine cavity 600 with a removal string 900 extending out of the uterine cavity 600.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. An inserter for an intrauterine system, the inserter comprising:
   an insertion tube having a first end and a second end, wherein the second end is opposite the first end and the first end is configured to removably receive an intrauterine system;
   a handle having a first end portion and a second end portion, wherein the second end portion is opposite the first end portion and the first end portion is coupled to the second end of the insertion tube, and wherein the handle comprises a handling mechanism for controlling movement of the insertion tube with respect to the intrauterine system; and
   an indicating mechanism operatively arranged in connection with the insertion tube and the handle, wherein the indicating mechanism is communicably coupled to the handling mechanism and is configured to provide indicative signals corresponding to operational stages of the inserter, and wherein the indicative signals comprise at least one light signal and the indicating mechanism comprises a power source.

2. The inserter of claim 1, the indicating mechanism comprising:
   at least one light source arranged in proximity to a connection of the first end portion of the handle and the second end of the insertion tube;
   a controller unit arranged in the handle, wherein the controller unit is configured to control the at least one light source to provide the at least one light signal corresponding to the operational stages of the inserter; and
   the power source is arranged in the handle to provide electrical power to the at least one light source and the controller unit.

3. The inserted of claim 2, wherein the at least one light source comprises at least one light emitting diode configured to emit visible light having at least one colour associated with the indicative signals.

4. The inserter of claim 3, wherein the at least one light emitting diode is configured to emit visible light having at least one colour continuously or intermittently.

5. The inserter of claim 2, wherein the power source is arranged as a detachable part of the handle of the inserter.

6. The inserter of claim 1, the operational stages comprising:
   retraction of the intrauterine system at least mainly within the insertion tube;
   insertion of the insertion tube into a uterine cavity of a uterus to a first insertion depth;
   a first movement of the insertion tube with respect to the intrauterine system;
   movement of the insertion tube to a second insertion depth; and
   a second movement of the insertion tube with respect to the intrauterine system, in order to release the intrauterine system.

7. The inserter of claim 6, wherein the indicating mechanism comprises at least one light source and the indicating mechanism is configured to:
   emit visible light having a first colour to indicate the intrauterine system is at least mainly retracted within the insertion tube;

emit the visible light having the first colour continuously to indicate insertion of the insertion tube into the uterine cavity of the uterus to the first insertion depth;

emit intermittently the visible light having the first colour during the first movement of the insertion tube;

emit a visible light having a second colour to indicate insertion of the insertion tube to the second insertion depth; and stop emitting the visible light having the second colour to indicate release of the intrauterine system in the uterine cavity.

8. The inserter of claims 6, wherein the intrauterine system is a T-shaped intrauterine system comprising two arms, the arms of the intrauterine system are released during the first movement of the insertion tube and the second insertion depth is such that the arms of the intrauterine system come into contact with fundus of uterine wall.

9. The inserter of claim 1, wherein the handling mechanism comprises a control button for controlling the movement of the insertion tube with respect to the intrauterine system.

10. The inserter of claim 9, wherein the control button comprises a slider button.

11. The inserter of claim 1, wherein the indicating mechanism comprises an audio source to provide the indicative signals corresponding to the operational stages of the inserter.

12. The inserter of claim 1, wherein the insertion tube comprises at least one optical fiber.

13. An inserter kit comprising:
an inserter for an intrauterine system comprising:
  an insertion tube having a first end and a second end, wherein the second end is opposite the first end and the first end is configured to removably receive an intrauterine system;
  a handle having a first end portion and a second end portion, wherein the second end portion is opposite the first end portion and the first end portion of the handle being coupled to the second end of the insertion tube, and wherein the handle comprises a handling mechanism for controlling movement of the insertion tube with respect to the intrauterine system; and
  an indicating mechanism operatively arranged in connection with the insertion tube and the handle, wherein the indicating mechanism is communicably coupled to the handling mechanism and configured to provide indicative signals corresponding to operational stages of the inserter, and wherein the indicative signals comprise at least one light signal;
a power source; and
a charging station comprising a charging dock configured to be removably coupled with the power source for charging the power source using a power supply.

14. The inserter kit of claim 13, wherein the power source is arranged in the handle.

15. The inserter kit of claim 13, wherein the power source is arranged as a detachable part of the handle.

* * * * *